US007750022B2

(12) United States Patent
Peters et al.

(10) Patent No.: US 7,750,022 B2
(45) Date of Patent: *Jul. 6, 2010

(54) QUINUCLIDINE DERIVATIVES AND THEIR PHARMACEUTICAL USE

(75) Inventors: Dan Peters, Ballerup (DK); Gunnar M. Olsen, Ballerup (DK); Elsebet Østergaard Nielsen, Ballerup (DK); Philip K. Ahring, Ballerup (DK); Tino Dyhring Jørgensen, Ballerup (DK); Michael R. Schrimpf, Grayslake, IL (US); Kevin B. Sippy, Antioch, IL (US)

(73) Assignees: Neurosearch A/S, Ballerup (DK); Abbott Laboratories, Abbott Park, IL (US)

( * ) Notice: Subject to any disclaimer, the term of this patent is extended or adjusted under 35 U.S.C. 154(b) by 972 days.

This patent is subject to a terminal disclaimer.

(21) Appl. No.: 10/568,148

(22) PCT Filed: Jun. 29, 2004

(86) PCT No.: PCT/EP2004/051283

§ 371 (c)(1),
(2), (4) Date: Jun. 9, 2006

(87) PCT Pub. No.: WO2005/016923

PCT Pub. Date: Feb. 24, 2005

(65) Prior Publication Data

US 2006/0217415 A1 Sep. 28, 2006

(30) Foreign Application Priority Data

Aug. 13, 2003 (WO) .................... PCT/DK03/00538

(51) Int. Cl.
*A61K 31/4745* (2006.01)
*C07D 453/02* (2006.01)
(52) U.S. Cl. ...................... 514/305; 546/133
(58) Field of Classification Search ................ 546/133; 514/305
See application file for complete search history.

(56) References Cited

U.S. PATENT DOCUMENTS

| 5,258,392 | A | 11/1993 | Wieringa et al. |
| 5,512,574 | A | 4/1996 | Husbands et al. |
| 5,589,477 | A | 12/1996 | Chokai et al. |
| 5,646,289 | A | 7/1997 | Alt et al. |
| 5,763,457 | A | 6/1998 | Bodick et al. |
| 5,852,037 | A | 12/1998 | Bodick et al. |
| 5,888,999 | A | 3/1999 | Bodick et al. |
| 5,948,793 | A | 9/1999 | Abreo et al. |
| 5,998,404 | A | 12/1999 | Merritt et al. |
| 2005/0171079 | A1* | 8/2005 | Schrimpf et al. ........ 514/210.01 |

FOREIGN PATENT DOCUMENTS

| EP | 0 458 214 A1 | 11/1991 |
| EP | 0 497 415 A1 | 8/1992 |
| EP | 0 555 478 A1 | 8/1993 |
| JP | 8-134067 A | 5/1996 |
| WO | WO-93/15073 A | 8/1993 |
| WO | WO-96/12711 A1 | 5/1996 |
| WO | WO-97/20819 A1 | 6/1997 |
| WO | WO-98/15551 A | 4/1998 |
| WO | WO-98/27983 A | 7/1998 |
| WO | WO-99/31097 A | 6/1999 |
| WO | WO-02/20521 A | 3/2002 |
| WO | WO-02/44176 A | 6/2002 |
| WO | WO-03/037896 A1 | 5/2003 |
| WO | WO-03/040147 A1 | 5/2003 |
| WO | WO-03/042210 A1 | 5/2003 |
| WO | WO-03/043991 A1 | 5/2003 |
| WO | WO-03/055878 A1 | 7/2003 |
| WO | WO-03/070728 A2 | 8/2003 |
| WO | WO-03/070731 A2 | 8/2003 |
| WO | WO-03/070732 A1 | 8/2003 |
| WO | WO-03/072578 A1 | 9/2003 |
| WO | WO-03/104227 A1 | 12/2003 |
| WO | WO-2004/016608 A | 2/2004 |
| WO | WO-2004/022556 A1 | 3/2004 |
| WO | WO-2004/076449 A2 | 9/2004 |

OTHER PUBLICATIONS

Perl et al., The FASEB journal : official publication of the Federation of American Societies for Experimental Biology, (Oct. 2003) vol. 17, No. 13, pp. 1948-1950.*
Database WPI Section CH, Week 199631, Derwent Publicaitons Ltd., London, GB; AN 1996-306548 EXP002297142.
George R. Brown et al., J. Med. Chem. 1999, vol. 42, No. 7, 1306-1311.

* cited by examiner

*Primary Examiner*—D. Margaret Seaman
*Assistant Examiner*—Niloofar Rahmani
(74) *Attorney, Agent, or Firm*—Birch, Stewart, Kolasch & Birch, LLP.

(57) ABSTRACT

This invention relates to novel quinuclidine derivatives and their use as pharmaceuticals. Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neurodegeneration, diseases or disorders related to inflammation, pain, and withdrawal symptoms caused by the termination of abuse of chemical substances.

7 Claims, No Drawings

QUINUCLIDINE DERIVATIVES AND THEIR PHARMACEUTICAL USE

TECHNICAL FIELD

This invention relates to novel quinuclidine derivatives and their use as pharmaceuticals. Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

BACKGROUND ART

The endogenous cholinergic neurotransmitter, acetylcholine, exerts its biological effect via two types of cholinergic receptors, the muscarinic Acetyl Choline Receptors (mAChR) and the nicotinic Acetyl Choline Receptors (nAChR).

It is well established that muscarinic acetylcholine receptors are of importance in relation to memory and cognition, and much research aimed at the development of agents for the treatment of memory related disorders have focused on the synthesis of muscarinic acetylcholine receptor modulators.

Indeed several CNS disorders can be attributed to a cholinergic deficiency, a dopaminergic deficiency, an adrenergic deficiency or a serotonergic deficiency.

Brown et al. [Brown et al.: Quinuclidine Inhibitors of 2,3-Oxidosqualene Cyclase-Lanosterol Synthase: Optimization from Lipid Profiles; *J. Med. Chem.* 1999 42 1306-1311] describe the synthesis of 3-substituted quinuclidine derivatives useful as inhibitors of the cholesterol biosynthesis. An effect on the nicotinic and/or the monoamine receptors is not reported.

SUMMARY OF THE INVENTION

The present invention is devoted to the provision of new quinuclidine derivatives that are modulators of the nicotinic and/or of the monoamine receptors, and which modulators are useful for the treatment of diseases or disorders related to the cholinergic receptors, and in particular the nicotinic acetylcholine receptor, the monoamine receptors, in particular the serotonin receptor (5-HTR), the dopamine receptor (DAR) and the norepinephrine receptor (NER), and of the biogenic amine transporters for serotonin (5-HT), dopamine (DA) and norepinephrine (NE).

Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

The compounds of the invention may also be useful as diagnostic tools or monitoring agents in various diagnostic methods, and in particular for in vivo receptor imaging (neuroimaging), and they may be used in labelled or unlabelled form.

Accordingly, in its first aspect the invention provides quinuclidine derivatives represented by Formula II

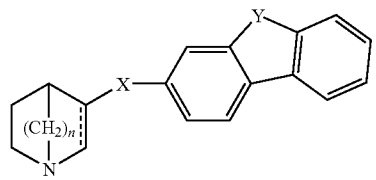

(II)

wherein,
===== represents an optional double bond;
n is 1, 2 or 3;
X represents a linker selected from —O—, —O—CH$_2$—, —O—CH$_2$—CH$_2$—, —S—, —SO—, —SO$_2$—, —CH$_2$—, —S—CH$_2$—CH$_2$—, —CH$_2$—, —C(=CH$_2$)—, —NH—, —N(alkyl)-, —C(=O)—, —C(=S)—,

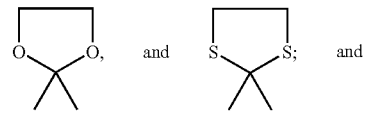

and

Y represents O, S, SO$_2$, or NR', wherein R' represents hydrogen or alkyl.

In another aspect the invention provides pharmaceutical compositions comprising a therapeutically effective amount of the quinuclidine derivative of the invention.

In a third aspect the invention relates to the use of the quinuclidine derivative of the invention, or a pharmaceutically-acceptable addition salt thereof, for the manufacture of a pharmaceutical composition/medicament for the treatment, prevention or alleviation of a disease or a disorder or a condition of a mammal, including a human, which disease, disorder or condition is responsive to the action of a nicotinic acetylcholine receptor modulator.

In a further aspect the invention provides a method of the treatment or alleviation of a disease or disorder of a living animal body, including a human, which disease or disorder is responsive to the action of a nicotinic acetylcholine receptor modulator, which method comprises the step of administering to such a living animal body, including a human, in need thereof a therapeutically effective amount of the quinuclidine derivative of the invention.

Other objects of the invention will be apparent to the person skilled in the art from the following detailed description and examples.

DETAILED DISCLOSURE OF THE INVENTION

Quinuclidine Derivatives

In a preferred embodiment the quinuclidine derivative of the invention is a compound of Formula II

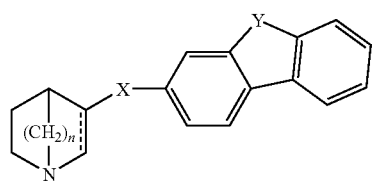

(II)

wherein
===== represents an optional double bond;
n is 1, 2 or 3;
X represents a linker selected from —O—, —O—CH$_2$—, —O—CH$_2$—CH$_2$—, —S—, —SO—, —SO$_2$—, —CH$_2$—, —S—CH$_2$—CH$_2$—, —CH$_2$—, —C(=CH$_2$)—, —NH—, —N(alkyl)-, —C(=O)—, —C(=S)—,

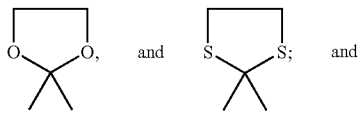

Y represents O, S, SO$_2$, or NR', wherein R' represents hydrogen or alkyl.

In a more preferred embodiment of this aspect the quinuclidine derivative of the invention is a compound of Formula II, wherein ===== represents a single (covalent) bond.

In another preferred embodiment of this aspect the quinuclidine derivative the invention is a compound of Formula II, wherein n is 1, 2 or 3.

In a third preferred embodiment of this aspect the quinuclidine derivative of the invention is a compound of Formula II, wherein X represents a linker selected from —O—, —O—CH$_2$—, —O—CH$_2$—CH$_2$—, —S—, and —CH$_2$—.

In a fourth preferred embodiment of this aspect the quinuclidine derivative of the invention is a compound of Formula II, wherein Y represents O, S, SO$_2$, or NR', wherein R' represents hydrogen or alkyl.

In a most preferred embodiment the quinuclidine derivative of the invention of Formula II is (±)-3-(Dibenzofuran-2-yloxy)-1-azabicyclo[2.2.2]octane;

or an enantiomer thereof, or a pharmaceutically-acceptable addition salt thereof, or an onium salt thereof.

Any combination of two or more of the embodiments described herein is considered within the scope of the present invention.

Definition of Substituents

In the context of this invention halo represents fluoro, chloro, bromo or iodo.

Thus a trihalomethyl group represents e.g. a trifluoromethyl group, a trichloromethyl group, and similar trihalo-substituted methyl groups.

In the context of this invention an alkyl group designates a univalent saturated, straight or branched hydrocarbon chain. The hydrocarbon chain preferably contain of from one to eighteen carbon atoms (C$_{1-18}$-alkyl), more preferred of from one to six carbon atoms (C$_{1-6}$-alkyl; lower alkyl), including pentyl, isopentyl, neopentyl, tertiary pentyl, hexyl and isohexyl. In a preferred embodiment alkyl represents a C$_{1-4}$-alkyl group, including butyl, isobutyl, secondary butyl, and tertiary butyl. In another preferred embodiment of this invention alkyl represents a C$_{1-3}$-alkyl group, which may in particular be methyl, ethyl, propyl or isopropyl.

In the context of this invention a cycloalkyl group designates a cyclic alkyl group, preferably containing of from three to seven carbon atoms (C$_{3-7}$-cycloalkyl), including cyclopropyl, cyclobutyl, cyclopentyl, cyclohexyl and cycloheptyl.

In the context of this invention a cycloalkyl-alkyl group designates a cycloalkyl group as defined above, which cycloalkyl group is substituted on an alkyl group as also defined above. Examples of preferred cycloalkyl-alkyl groups of the invention include cyclopropylmethyl and cyclopropylethyl.

In the context of this invention an alkoxy group designates an "alkyl-O—" group, wherein alkyl is as defined above. Examples of preferred alkoxy groups of the invention include methoxy and ethoxy.

In the context of this invention a hydroxy-alkoxy group designates an alkoxy group as defined above, which alkoxy group is substituted with one or more hydroxy groups. Preferred hydroxy-alkoxy groups of the invention include 2-hydroxy-ethoxy, 3-hydroxy-propoxy, 4-hydroxy-butoxy, 5-hydroxy-pentoxy and 6-hydroxy-hexoxy.

In the context of this invention a cycloalkoxy group designates a "cycloalkyl-O-" group, wherein cycloalkyl is as defined above.

In the context of this invention an alkoxy-alkyl group designates an "alkyl-O-alkyl-" group, wherein alkyl is as defined above. Examples of preferred alkoxy-alkyl groups of the invention include methoxy-methyl, methoxy-ethyl, ethoxy-methyl, and ethoxy-ethyl.

In the context of this invention an alkoxy-alkoxy group designates an "alkyl-O-alkyl-O—" group, wherein alkyl is as defined above. Examples of preferred alkoxy-alkoxy groups of the invention include methoxy-methoxy, methoxy-ethoxy, ethoxy-methoxy, and ethoxy-ethoxy.

In the context of this invention a cycloalkoxy-alkyl group designates a "cycloalkyl-O-alkyl" group, wherein cycloalkyl and alkyl are as defined above.

In the context of this invention a cycloalkoxy-alkoxy group designates a "cycloalkyl-O-alkyl-O—" group, wherein cycloalkyl and alkyl are as defined above.

In the context of this invention a mono- or polycyclic carbocyclic group is a mono- or polycyclic carbocyclic group holding carbon only as ring atom. The ring structure may in particular be aromatic (i.e. an aryl group), or saturated or partially saturated.

Preferred mono- or polycyclic carbocyclic groups of the invention include phenyl; indanyl, in particular 4-indanyl and 5-indanyl; indenyl, in particular 1-indenyl, 2-indenyl and 3-indenyl; naphthyl, in particular 1-naphthyl and 2-naphthyl; 5,6,7,8-tetrahydro-naphthyl, in particular 5,6,7,8-tetrahydro-1-naphthyl and 5,6,7,8-tetrahydro-2-naphthyl; azulenyl, in particular 1-azulenyl, 2-azulenyl and 3-azulenyl; fluorenyl, in particular 1-fluorenyl, 2-fluorenyl, 3-fluorenyl and 4-fluorenyl; and anthracenyl, in particular 1-anthracenyl and 2-anthracenyl.

The mono- or polycyclic carbocyclic group may in particular be an aromatic group (aryl). Preferred aryl groups of the invention include phenyl; indenyl, in particular 1-indenyl, 2-indenyl and 3-indenyl; naphthyl, in particular 1-naphthyl and 2-naphthyl; azulenyl, in particular 1-azulenyl, 2-azulenyl and 3-azulenyl; and anthracenyl, in particular 1-anthracenyl and 2-anthracenyl.

In the context of this invention a mono- or polycyclic heterocyclic group is a mono- or polycyclic compound, which holds one or more heteroatoms in its ring structure. The term poly-heterocyclic groups includes benzo-fused five- and six-membered heterocyclic rings containing one or more heteroatoms. Preferred heteroatoms include nitrogen (N), oxygen (O), and sulphur (S). One or more of the ring structures may in particular be aromatic (i.e. a heteroaryl).

Preferred monocyclic heterocyclic groups of the invention include pyridyl, in particular pyrid-2-yl, pyrid-3-yl and pyrid-4-yl; thienyl, in particular thien-2-yl and thien-3-yl; furanyl, in particular furan-2-yl and furan-3-yl; pyridazinyl, in particular pyridazin-3-yl and pyridazin-4-yl; thiazolyl, in particular thiazol-2-yl, thiazol-4-yl and thiazol-5-yl; and thiadiazolyl, in particular 1,3,4-thiadiazol-2-yl, 1,3,4-thiadiazol-5-yl, 1,2,4-thiadiazol-3-yl and 1,2,4-thiadiazol-5-yl.

Preferred polycyclic heterocyclic of the invention include indolyl, in particular indol-2-yl and indol-3-yl; isoindolyl, in particular isoindol-2-yl; quinolinyl, in particular quinolin-2-yl, quinolin-3-yl, quinolin-4-yl, quinolin-5-yl and quinolin- 6-yl; quinoxalinyl, in particular quinoxalin-2-yl and quinoxalin-3-yl; benzimidazolyl, in particular benzimidazol-2-yl; benzoxazolyl, in particular benzoxazol-2-yl; benzthiazolyl, in particular benzthiazol-2-yl; benzisothiazolyl, in particular benzisothiazol-3-yl; benztriazolyl, in particular 1,2,3-benztriazol-1-yl; imidazo[1,2-b]pyridazinyl, in particular imidazo[1,2-b]pyridazin-6-yl; and dibenzofuranyl, in particular dibenzofuran-2-yl.

Pharmaceutically Acceptable Salts

The quinuclidine derivative of the invention may be provided in any form suitable for the intended administration. Suitable forms include pharmaceutically (i.e. physiologically) acceptable salts, and pre- or prodrug forms of the quinuclidine derivative of the invention.

Examples of pharmaceutically acceptable addition salts include, without limitation, the non-toxic inorganic and organic acid addition salts such as the hydrochloride derived from hydrochloric acid, the hydrobromide derived from hydrobromic acid, the nitrate derived from nitric acid, the perchlorate derived from perchloric acid, the phosphate derived from phosphoric acid, the sulphate derived from sulphuric acid, the formate derived from formic acid, the acetate derived from acetic acid, the aconate derived from aconitic acid, the ascorbate derived from ascorbic acid, the benzenesulphonate derived from benzensulphonic acid, the benzoate derived from benzoic acid, the cinnamate derived from cinnamic acid, the citrate derived from citric acid, the embonate derived from embonic acid, the enantate derived from enanthic acid, the fumarate derived from fumaric acid, the glutamate derived from glutamic acid, the glycolate derived from glycolic acid, the lactate derived from lactic acid, the maleate derived from maleic acid, the malonate derived from malonic acid, the mandelate derived from mandelic acid, the methanesulphonate derived from methane sulphonic acid, the naphthalene-2-sulphonate derived from naphtalene-2-sulphonic acid, the phthalate derived from phthalic acid, the salicylate derived from salicylic acid, the sorbate derived from sorbic acid, the stearate derived from stearic acid, the succinate derived from succinic acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

Examples of pharmaceutically acceptable cationic salts of a chemical compound of the invention include, without limitation, the sodium, the potassium, the calcium, the magnesium, the zinc, the aluminium, the lithium, the choline, the lysine, and the ammonium salt, and the like, of a chemical compound of the invention containing an anionic group. Such cationic salts may be formed by procedures well known and described in the art.

In the context of this invention the "onium salts" of N-containing compounds are also contemplated as pharmaceutically acceptable salts (aza-onium salts). Preferred aza-onium salts include the alkyl-onium salts, in particular the methyl- and the ethyl-onium salts; the cycloalkyl-onium salts, in particular the cyclopropyl-onium salts; and the cycloalkylalkyl-onium salts, in particular the cyclopropyl-methyl-onium salts.

Steric Isomers

The quinuclidine derivatives of the present invention may exist in (+) and (−) forms as well as in racemic forms (±). The racemates of these isomers and the individual isomers themselves are within the scope of the present invention.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l- (tartrates, mandelates, or camphorsulphonate) salts for example.

The quinuclidine derivatives of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in *"Enantiomers, Racemates, and Resolutions"*, John Wiley and Sons, New York (1981).

Optical active compounds can also be prepared from optical active starting materials.

Methods of Preparation

The quinuclidine derivatives of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Biological Activity

The present invention relates to novel quinuclidine derivatives, which are found to be cholinergic ligands at the nicotinic acetylcholine receptors (nAChR), and modulators of the monoamine receptors, in particular the biogenic amine transporters such as the serotonin receptor (5-HTR), the dopamine receptor (DAR) and the norepinephrine receptor (NER), and of the biogenic amine transporters for serotonin (5-HT), dopamine (DA) and norepinephrine (NE). Also preferred quinuclidine derivatives of the invention show selective α7 activity, as shown in the working examples. The compounds of the present invention may in particular be agonists, partial agonists, antagonists and allosteric modulators of the receptor.

Due to their pharmacological profile the quinuclidine derivatives of the invention may be useful for the treatment of diseases or conditions as diverse as CNS related diseases, PNS related diseases, diseases related to smooth muscle contraction, endocrine disorders, diseases related to neuro-degeneration, diseases related to inflammation, pain, and withdrawal symptoms caused by the termination of abuse of chemical substances.

In a preferred embodiment the quinuclidine derivatives of the invention are used for the treatment of diseases, disorders, or conditions relating to the central nervous system. Such diseases or disorders includes anxiety, cognitive disorders, learning deficit, memory deficits and dysfunction, Alzheimer's disease, attention deficit, attention deficit hyperactivity disorder (ADHD), Parkinson's disease, Huntington's disease, Amyotrophic Lateral Sclerosis, Gilles de la Tourette's syndrome, psychosis, depression, mania, manic depression, schizophrenia, obsessive compulsive disorders (OCD), panic disorders, eating disorders such as anorexia nervosa, bulimia and obesity, narcolepsy, nociception, AIDS-dementia, senile dementia, periferic neuropathy, autism, dyslexia, tardive dyskinesia, hyperkinesia, epilepsy, bulimia, post-traumatic syndrome, social phobia, sleeping disorders, pseudodementia, Ganser's syndrome, pre-menstrual syndrome, late luteal phase syndrome, chronic fatigue syndrome, mutism, trichotillomania, and jet-lag.

In a preferred embodiment diseases, disorders, or conditions relating to the central nervous system for which the quinuclidine derivatives of the invention are used are cognitive disorders, psychosis, schizophrenia and/or depression.

In another preferred embodiment the quinuclidine derivatives of the invention may be useful for the treatment of diseases, disorders, or conditions associated with smooth muscle contractions, including convulsive disorders, angina pectoris, premature labour, convulsions, diarrhoea, asthma, epilepsy, tardive dyskinesia, hyperkinesia, premature ejaculation, and erectile difficulty.

In yet another preferred embodiment the quinuclidine derivatives of the invention may be useful for the treatment of endocrine disorders, such as thyrotoxicosis, pheochromocytoma, hypertension and arrhythmias.

In still another preferred embodiment the quinuclidine derivatives of the invention may be useful for the treatment of neurodegenerative disorders, including transient anoxia and induced neurodegeneration.

In even another preferred embodiment the quinuclidine derivatives of the invention may be useful for the treatment of inflammatory diseases, disorders, or conditions, including inflammatory skin disorders such as acne and rosacea, Chron's disease, inflammatory bowel disease, ulcerative colitis, and diarrhoea.

In still another preferred embodiment the quinuclidine derivatives of the invention may be useful for the treatment of mild, moderate or even severe pain of acute, chronic or recurrent character, as well as pain caused by migraine, postoperative pain, and phantom limb pain. The pain may in particular be neuropathic pain, chronic headache, central pain, pain related to diabetic neuropathy, to post therapeutic neuralgia, or to peripheral nerve injury.

Finally the quinuclidine derivatives of the invention may be useful for the treatment of withdrawal symptoms caused by termination of use of addictive substances. Such addictive substances include nicotine containing products such as tobacco, opioids such as heroin, cocaine and morphine, benzodiazepines and benzodiazepine-like drugs, and alcohol. Withdrawal from addictive substances is in general a traumatic experience characterised by anxiety and frustration, anger, anxiety, difficulties in concentrating, restlessness, decreased heart rate and increased appetite and weight gain.

In this context "treatment" covers treatment, prevention, prophylactics and alleviation of withdrawal symptoms and abstinence as well as treatment resulting in a voluntary diminished intake of the addictive substance.

In another aspect, the quinuclidine derivatives of the invention are used as diagnostic agents, e.g. for the identification and localisation of nicotinic receptors in various tissues.

Pharmaceutical Compositions

In another aspect the invention provides novel pharmaceutical compositions comprising a therapeutically effective amount of the quinuclidine derivatives of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the quinuclidine derivative together with one or more pharmaceutically acceptable carriers therefore, and, optionally, other therapeutic and/or prophylactic ingredients, know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in drage, in powder, or in liquid form, and parenteral administration, in particular cutaneous, subcutaneous, intramuscular, or intravenous injection. The pharmaceutical composition of the invention can be manufactured by a person skilled in the art by use of standard methods and conventional techniques appropriate to the desired formulation. When desired, compositions adapted to give sustained release of the active ingredient may be employed.

Further details on techniques for formulation and administration may be found in the latest edition of *Remington's Pharmaceutical Sciences* (Maack Publishing Co., Easton, Pa.).

The actual dosage depend on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day isv., and from about 1 µg/kg to about 100 mg/kg/day p.o.

Methods of Therapy

Due to their pharmacological profile the compounds of the invention may be useful for the treatment of diseases or conditions as diverse as CNS related diseases, PNS related diseases, diseases related to smooth muscle contraction, endocrine disorders, diseases related to neuro-degeneration, diseases related to inflammation, pain, and withdrawal symptoms caused by the termination of abuse of chemical substances.

In another aspect the invention provides methods of the treatment, prevention or alleviation of diseases or disorders or conditions of a living animal body, including a human, which disease or disorder is responsive to the action of a monoamine receptor modulator, and which method comprises the step of administering to such a living animal body, including a human, in need thereof a therapeutically effective amount of the quinuclidine derivative of the invention.

In the context of this invention the term "treating" covers treatment, prevention, prophylaxis or alleviation, and the term "disease" covers illnesses, diseases, disorders and conditions related to the disease in question.

It is at present contemplated that a suitable dosage lies within the range of from about 0.1 to about 500 milligram of active substance daily, more preferred of from about 10 to about 70 milligram of active substance daily, administered once or twice a day, dependent as usual upon the exact mode of administration, form in which administered, the indication toward which the administration is directed, the subject involved and the body weight of the subject involved, and further the preference and experience of the physician or veterinarian in charge.

EXAMPLES

The invention is further illustrated with reference to the following examples, which are not intended to be in any way limiting to the scope of the invention as claimed.

General remarks: All reactions involving air sensitive reagents or intermediates were performed under nitrogen and in anhydrous solvents. Magnesium sulfate was used as drying agent in the workup-procedures and solvents were evaporated under reduced pressure.

Method G (±)-3-(Dibenzofuran-2-yloxy)-1-azabicyclo[2.2.2]octane Fumaric Acid Salt (Compound G1)

To a mixture of (±)-3-quinuclidinol (3.0 g, 23.6 mmol), 2-hydroxydibenzofuran (4.3 g, 23.6 mmol), triphenylphosphine (9.29 g, 35.4 mmol) and THF, was added: diethylazodicarboxylate (6.3 ml, 35.4 mmol) over a time period of 40 min at room temperature. The mixture was stirred at 50° C. for 7 days. Aqueous sodium hydroxide (100 ml, 1 M) was added. The mixture was extracted with dichloromethane (3×100 ml). Chromatography on silica gel with dichloromethane, methanol and conc. ammonia (89:10:1) gave the title compound. Yield 2.0 g (29%).

The corresponding fumaric acid salt was obtained by addition of a diethyl ether and methanol mixture (9:1) saturated with fumaric acid. Mp 131.3-133.8° C.

The compound also may be named (±)-3-(Dibenzofuran-2-yloxy)-quinuclidine.

The invention claimed is:

1. A quinuclidine derivative represented by Formula II

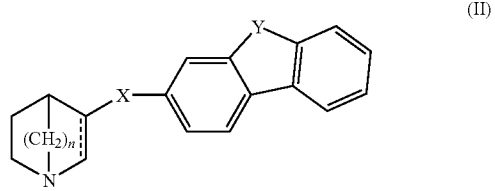

(II)

wherein
----- represents an optional double bond;
n is 1, 2 or 3;
X represents a linker selected from —O—, —S—, —SO—, —SO$_2$—, —CH$_2$—, —C(=CH$_2$)—, —NH—, —N(alkyl)-, —C(=O)—, —C(=S)—,

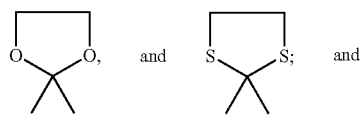

Y represents O, S, SO$_2$, or NR', wherein R' represents hydrogen or alkyl.

2. The quinuclidine derivative of claim 1, wherein ----- represents a single (covalent) bond.

3. The quinuclidine derivative of claim 1, wherein n is 1, 2 or 3.

4. The quinuclidine derivative of claim 1, wherein X represents a linker selected from —O—, —S—, and —CH$_2$—.

5. The quinuclidine derivative of claim 1, wherein Y represents O, S, SO$_2$, or NR', wherein R' represents hydrogen or alkyl.

6. The quinuclidine derivative of claim 5, which is
(±)-3-(Dibenzofuran-2-yloxy)-1-azabicyclo[2.2.2]octane;
or an enantiomer thereof, or a pharmaceutically-acceptable addition salt thereof, or an onium salt thereof.

7. A pharmaceutical composition comprising a therapeutically effective amount of a quinuclidine derivative of claim 1, or a pharmaceutically-acceptable addition salt thereof.

* * * * *